United States Patent [19]

Freeman et al.

[11] 4,019,373
[45] Apr. 26, 1977

[54] ULTRASONIC TRANSDUCER MOUNTING AND COUPLING ASSEMBLY

[75] Inventors: David Lewis Freeman, Bridgenorth; Ralph Seymour Flemons, Peterborough, both of Canada

[73] Assignee: Canadian General Electric Company Limited, Toronto, Canada

[22] Filed: May 28, 1975

[21] Appl. No.: 581,636

[30] Foreign Application Priority Data

June 17, 1974 Canada .................................. 202680

[52] U.S. Cl. .......................... 73/71.5 US; 73/194 A
[51] Int. Cl.² ........................................ G01N 29/00
[58] Field of Search ................. 73/71.5 US, 194 A; 310/8.2, 8.3, 9.1, 8.7

[56] References Cited

UNITED STATES PATENTS

| | | | |
|---|---|---|---|
| 3,242,723 | 3/1966 | Evans | 73/71.5 US |
| 3,394,586 | 7/1968 | Cross | 73/71.5 US |
| 3,580,092 | 5/1971 | Scarpa | 73/194 B |
| 3,663,842 | 5/1972 | Miller | 310/8.3 |
| 3,789,656 | 2/1974 | Miller | 73/71.5 US |

Primary Examiner—Charles A. Ruehl
Attorney, Agent, or Firm—R. A. Eckersley

[57] ABSTRACT

An ultrasonic transducer apparatus for sensing flow velocity through a pipe wall has a pair of strap-on transducer assemblies for securing to an unprepared pipe surface, the energy coupling between each transducer unit and the pipe or other working device being provided by an elastomeric contact pad, which also facilitates rapid replacement of the transducer crystal, by simplified assembly.

5 Claims, 3 Drawing Figures

ULTRASONIC TRANSDUCER MOUNTING AND COUPLING ASSEMBLY

The present invention relates to ultrasonic transducer coupling devices in which a piezo electric or ferro-electric material is used to convert electrical energy into mechanical energy and vice versa.

Conventional ultrasonic transducers generally comprise a disc of piezo or ferro-electric material, either monocrystalline such as quartz or polycrystalline such as lead-zirconate-titanate. The front and rear faces of this disc are metallized, commonly, with silver to provide electrodes for electrical connection with the crystal. Connections to these faces are usually made by soldering a wire to the metallized face, by attaching a conductor by use of a conductive cement or by clamping the face firmly to a metal rim, commonly part of the mounting structure.

The most common use of such transducers is to produce pulses of acoustic (usually ultrasonic) energy which are transmitted into metal or plastic bodies for purposes of measuring their thickness or detecting hidden flaws in their interior. For pulse transmission and reception it is usual to couple to the rear surface of the disc a backing material having a selected ballasting mass and loss characteristics to damp the crystal resonances and improve its pulse response.

The transducer coupling arrangement according to the present invention normally used in energy coupling relation to generate and transmit continuous ultrasonic vibrations into a pipe and to receive such vibrations on the opposite wall of the pipe, as part of an ultrasonic cross-correlation flowmeter. However, it will be apparent that the presently disclosed features and characteristics also make it suitable for other utilization.

To efficiently couple ultrasonic energy from a piezo electric disc to another solid object, it is important to replace the air between the disc and the surface of the object with a medium having an acoustic impedance moderately close to that of the disc and the object. Conventional practice is to use, for this coupling medium, a liquid, a grease or a cement. When the coupled system is required to remain stable for long periods of time under varying temperatures, each of these prior coupling systems has deficiencies. Thus liquids require to be contained and may leak, grease may flow and often contains undetectable air bubbles, which impede effective coupling, while cement may crack or may transmit stresses to the disc causing it to crack.

A conventional transducer assembly usually requires the provision of soldering of wires to the faces of the piezo disc, cementing of the disc in place and bonding of the backing ballast material to the disc. Each of these processes make it impossible or very difficult to replace the disc of a transducer assembly and usually necessitates the replacement of the entire assembly in the event that the disc is defective or has a resonant frequency unsuitable for a particular application.

It is an object of the present invention to produce a transducer assembly which is particularly suitable to couple continuous-wave ultrasonic energy to or from a cylindrical or plane surface, with the capability of: conforming to an unprepared or somewhat irregular surface contour and of providing consistent coupling over long periods of time despite vibration and temperature changes.

A further object of the invention is the provision of a transducer coupling permitting ready replacement of the transducer element or disc without damage to the disc or the coupling assembly.

A further object is the provision of a transducer coupling assembly which may be simply mounted with its energy coupling axis normal to the mounting surface without mechanical modification of that surface.

Certain embodiments of the invention are described, reference being made to the accompanying drawings, wherein.

Figure 2:
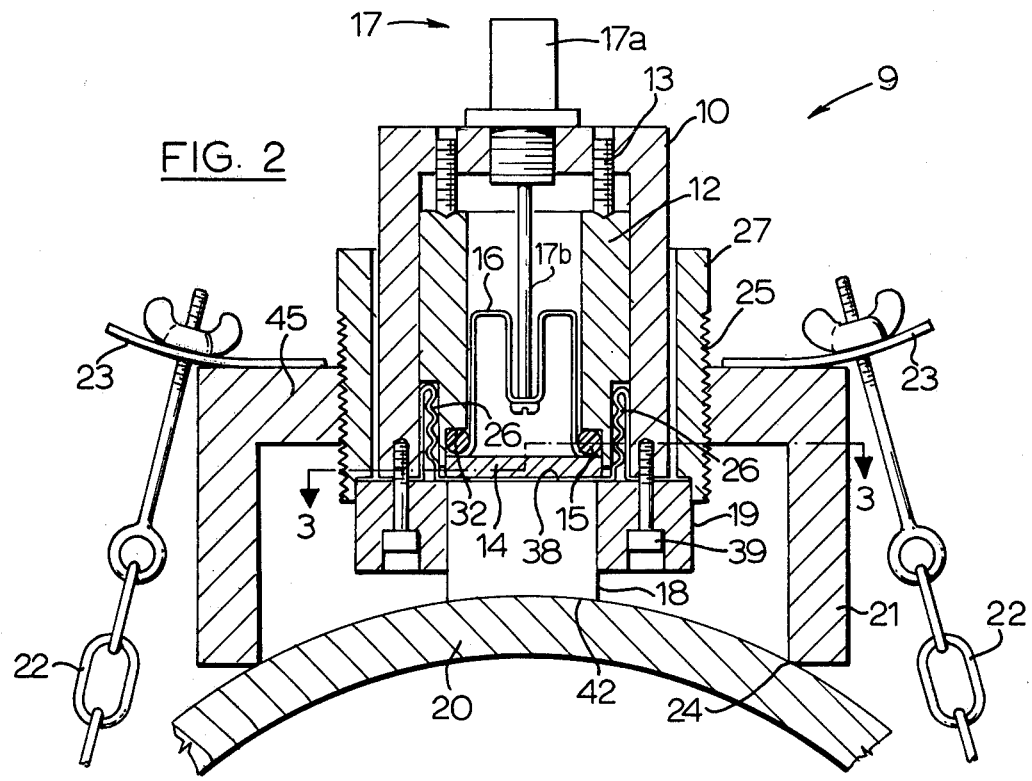
FIG. 2 is a section taken at 2—2 of FIG. 1.
Figure 3:
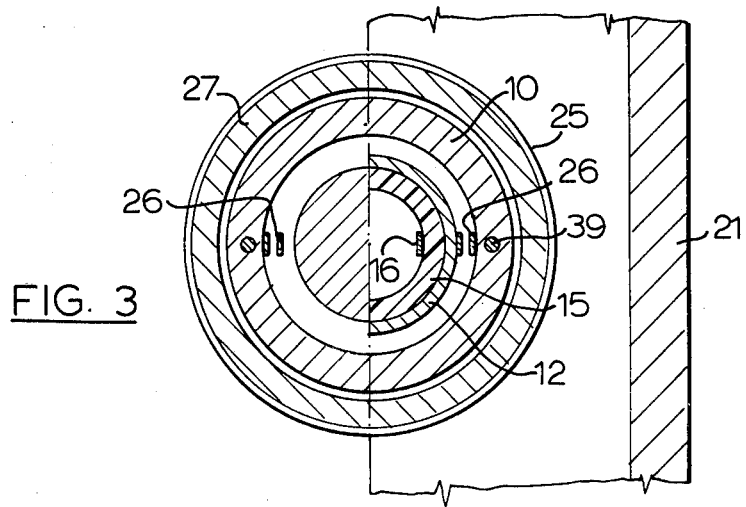
FIG. 3 is a section taken at 3—3 of FIG. 2.

Referring to FIG. 2, the transducer coupling assembly 9 consists of an electrically conductive casing of tubular form 10 having an electrically insulating liner 12 which will remain coaxial with the casing but may be forced axially forward by set screws 13. The front face of the liner 12 is provided with a recess 32 which will accommodate a suitable piezo-electric or ferro-electric disc 14 which is metallized on its front and rear surfaces, and an elastomeric O-ring 15.

Thin compliant metal strips 16 are provided which are pressed against the rear surface of disc 14 by the O-ring and serve to make electrical contact with the metallized face of the disc 14. A coaxial electrical connector 17 is mounted in the casing 10, its outer or shield connection 17a being connected to the casing, its inner contact 17b serving to mount the strips 16 by way of a screw and hence providing electrical connection between the metallized rear surface of the disc 14 and the connector 17.

A coupling block 18 of silicone rubber is provided which is moulded within a ring of insulating material 19. The rear surface of the ring 19 is held against the open end of casing 10 by means of cap screws 39. The rear surface 38 of the coupling block 18 protrudes slightly from the rear surface of the ring 19 and rests against the front face of the piezo disc 14. The front surface 42 of the coupling block 18 protrudes, typically 1/8 inch from the ring and is held in contact with the pipe 20 or other body to which the ultrasonic energy is to be coupled.

A second series of thin compliant metal strips 26, typically of 0.002 inch thick material, are provided. One end of each strip 26 is clamped between the periphery of the front metallized surface of the disc 14 and the inner face of the coupling block 18. The other end of each strip is clamped between the ring 19 and the metal casing 10. These strips provide multiple electrical paths from the front metallized surface of the disc to the metal casing and thence to the shell of the connector 17.

Figure 1:
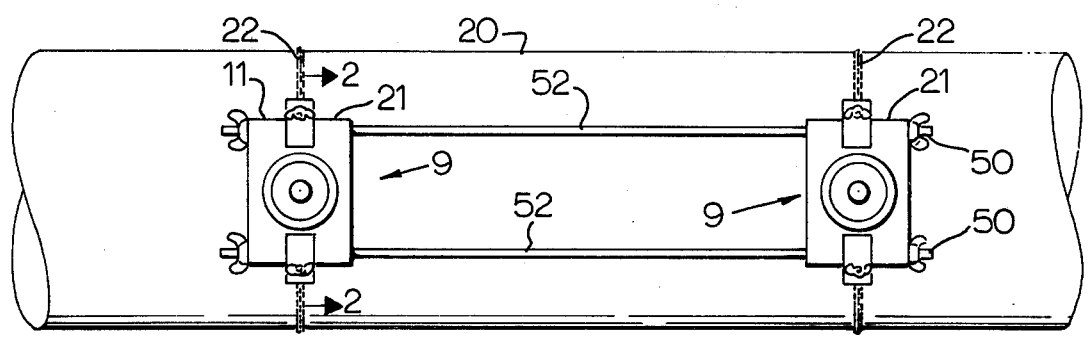
FIG. 1 is a plan view of a strap-on assembly incorporating a pair of transducer couplings in longitudinally spaced relation, mounted on a pipe by means in accordance with the present invention.

Referring also to FIG. 1, the casing 10, its disc and coupling block assembly is secured in tight contact with a pipe 20, by a U shaped channel member 21. Chains 22 and tensioning springs 23 are provided to force the inner corners 24 of the channel into line contact with the cylindrical pipe 20, ensuring that the web portion 45 of the channel is in a plane normal to a diameter of the pipe. A cylindrical guide 27 is provided in the channel section to hold the casing 10 at right angles to the surface of pipe 20. Adjusting means such as a screw thread 25 allows the guide 27 to be positioned axially in the casing 10. Axial force is transmitted to the casing 10 so that the coupling block 18 is forced against the pipe 20 and deformed sufficiently to ensure substantial conformity and provide effective contact around the curved pipe surface. To maintain electrical insulation between the casing 10 and the wall of pipe 20 the guide 25 presses on the insulating ring 19 and does not contact the casing 10.

Referring to FIG. 1, a pair of assemblies 9 comprising a transducer combination 48 are mounted on rods 50, having spacers 52 between the assemblies 9 for a desired centre-to-centre spacing.

To further enhance the coupling for ultrasonic energy beween the disc and the pipe a small amount of viscous liquid (e.g. that trademarked VISCASIL 10,000, product of the General Electric Company) is placed on each face of the coupling block 18. This further serves to exclude the air and remains in place by capillary attraction.

For use with an ultrasonic cross-correlation flow metering system two identical transducer combination assemblies 48 are used. One combination assembly 48 having a pair of transducer couplings 9 is mounted in diametrically opposite position with another assembly 48 at one axial location on a pipe 20. Chains 22 may be common to both assemblies.

The advantages of this arrangement over the previous art include:

1. The coupling path between the transducer disc 14 and pipe wall 20 is efficient, easy to assemble and stable for indefinite periods.

2. The coupling block 18 can be removed from the pipe 20 without breaking an adhesive bond and can be subsequently replaced in exactly the sme position if the channel member 21 remains fixed.

3. By removing the coupling block and ring subassembly from the casing 10 the piezo disc 14 can be replaced without breaking soldered or cemented electrical connections. The multiple contact strips clamped to the disc under resilient pressure ensure reliable electrical connections. This permits substitution of transducer elements 14 having differing desired characteristics in relation to the pipe 20 and its contents.

4. The entire assembly 48 can be rapidly mounted on a pipe 20 without preparation of the mounting site, and can be easily removed and remounted in a new location.

5. Electrical isolation between the transducers 14 and the pipe wall 20 is achieved with a consequent avoidance of "ground-loops" between the various circuits.

6. The use of thin metal strips 16, 26 clamped to the transducer 14 at the disc faces by pressure from resilient pressure members such as the O-ring 15 and coupling block 18 avoids distortion of the disc 14 which can result from its being clamped to a metal rim. The use of resilient contact inducing presser ring 15 and coupling block 18 also avoids the need to use solder which can affect the acoustic symmetry of the disc due to the added mass and/or due to local depolarization caused by the heat of soldering.

What I claim as new and desire to secure by Letters Patent of the United States is:

1. A transducer coupling for providing electromechanical energy coupling with a pipe, comprising; adjustable mounting means for attaching said coupling to said pipe, having casing means secured thereto in spaced relation from the pipe when installed, a resilient elastomeric coupling member, securing means holding said coupling member is attached relation to the casing means, having an outer end of said coupling member projecting therefrom to contact the surface of said pipe in compressed relation therewith, a transducer having one surface thereof secured in compressed relation against the other end of said coupling member, by way of electrically insulated mounting means, first and second electrical connections to said transducer, said first connection contacting said one surface of the transducer, being held in contacting relation therewith by compressive force acting between said coupling member and said insulated mounting means, said insulated mounting means securing said second connection in resilient contacting relation to a second face of said transducer.

2. The transducer coupling as claimed in claim 1, said coupling member securing means including an insulating ring securing said coupling member in compressed relation with said casing means, and fastening means removably securing said insulating ring to the casing means to permit removal of the ring and coupling member, to provide ready access to said transducer for purposes of replacement.

3. The transducer coupling as claimed in claim 1, said insulating ring securing said first electrical connection to said transducer one surface and to an electrically conducting portion of said casing.

4. The transducer coupling as claimed in claim 2 including adjustable loading means to adjustably vary the position of said insulated mounting means relative to said casing, for controlling the force securing said second connection to said transducer.

5. The coupling as claimed in claim 1 in combination with a second said transducer coupling secured to said mounting means in predetermined axially spaced relation from the first said coupling relative to said pipe.

* * * * *